United States Patent [19]

Wilczek et al.

[11] Patent Number: 5,719,251

[45] Date of Patent: Feb. 17, 1998

[54] REACTIVE ORGANOSILICON COMPOUNDS

[75] Inventors: Lech Wilczek, Wilmington, Del.; Idisor Hazan, Clementon, N.J.; Basil V. Gregorovich, Wilmington, Del.

[73] Assignee: E. I. du Pont de Nemours and Company, Wilmington, Del.

[21] Appl. No.: 703,285

[22] Filed: Aug. 26, 1996

Related U.S. Application Data

[63] Continuation-in-part of Ser. No. 400,725, Mar. 8, 1995, abandoned.

[51] Int. Cl.$^6$ .................................................. C08G 77/04
[52] U.S. Cl. .................... 528/35; 556/443; 556/444; 556/432; 556/431; 556/438; 556/440; 427/387
[58] Field of Search ................................ 556/443, 444, 556/432, 431, 438, 440; 528/35; 427/387

[56] References Cited

U.S. PATENT DOCUMENTS

| | | | |
|---|---|---|---|
| 2,545,780 | 3/1951 | Hatcher et al. | 260/448.2 |
| 2,924,588 | 2/1960 | Speier | 260/46.5 |
| 3,994,947 | 11/1976 | Bond, Jr. et al. | 260/448.2 Q |
| 4,281,145 | 7/1981 | Mitchell | 556/440 |
| 4,408,011 | 10/1983 | Barnabeo | 525/100 |
| 4,642,356 | 2/1987 | Langner et al. | 549/214 |
| 4,645,850 | 2/1987 | Deschler et al. | 556/431 |
| 4,647,682 | 3/1987 | Panster et al. | 556/431 |
| 4,965,334 | 10/1990 | Mohr et al. | 528/34 |
| 5,266,670 | 11/1993 | Nakos et al. | 528/32 |
| 5,527,936 | 6/1996 | Dindi et al. | 556/479 |
| 5,530,152 | 6/1996 | Dindi et al. | 556/479 |

FOREIGN PATENT DOCUMENTS 558576  6/1958  Canada.

OTHER PUBLICATIONS

Petrov, A.D. et al, "The Preparation of Organosilicon Derivatives of Bicyclo-(2,2,1)-Heptane", translated from *Zhurnal Obshchel Khimii*, 31 (4), 1109–1117 (1961).

Marciniec, B. et al, *Comprehensive Handbook on Hydrosilation*, Pergamon Press, Oxford, pp. 35–153 (1992).

Walbridge, DJ, Editor, *Science and Technology of Polymer Colloids*, 1, 40–50 (1983).

Lukevits, E.Y. et al, *Organic Insertion Reactions of Group IV Elements*, Consultants Bureau, New York, pp. 38–40 (1966).

Greber, G., *Die Makromol. Chem.*, 53, 192–196 (1962).

*Primary Examiner*—Margaret W. Glass

[57] ABSTRACT

Organosilicon compounds are described which contain a cyclic organic moiety between at least two reactive silane groups. The compounds are useful in coatings, adhesives, and sealants, and the like.

14 Claims, No Drawings

REACTIVE ORGANOSILICON COMPOUNDS

CROSS-REFERENCE TO RELATED APPLICATION

This is a continuation-in-part of application Ser. No. 08/400,725 filed Mar. 8, 1995, now abandoned.

FIELD OF THE INVENTION

Organosilicon compounds are described which contain a cyclic organic moiety between reactive silane groups. The compounds are useful in coatings, adhesives, and the like.

TECHNICAL BACKGROUND

Reactive organosilicon compounds have found widespread use as coupling agents between organic and inorganic materials, for example, in adhesives, sealants, and coatings. Such compounds have found use in, for example, maintenance coatings, automotive coatings and architectural coatings.

Of particular interest to makers and users of coatings is to lower the volatile organic content (VOC) of such coatings, particularly to meet increasingly stringent environmental regulations. Various possible approaches for solving VOC problems are, therefore, of significant interest in the relevant industries.

Applicants have found that lower VOC compositions can be obtained by the use of certain novel reactive organosilicon compounds.

SUMMARY OF THE INVENTION

This invention concerns a compound of the formula

wherein:

A is an organic radical, which is selected from the group consisting of (a) carbocyclic groups which are either cycloaliphatic or aromatic and (b) two carbocyclic groups which are either cycloaliphatic or aromatic, connected to each other through a covalent bond, or through an alkylene group of 1 to 5 carbon atoms, or through a heteroatom, or fused rings in which two rings share two or more carbon atoms between them;

with y free valencies, each of which free valencies is to a different carbon atom of any carbocyclic ring formed by A; provided that when A belongs to the above group (b), at least two such valencies are attached to two different rings, each B is independently a substituted alkylene group that is substituted with at least one ether oxygen atom and/or at least one ester group, wherein the silicon atom is separated from the oxygen atom by at least two carbon atoms, and wherein the oxygen atom or the ester group, present as a —C(O)OR$^3$— or —O(O)CR$^3$— group, are connected directly to A or indirectly to A through an alkylene segment, each such B which is substituted with an ester group having 3–20 carbon atoms; each such B which is substituted with the ether oxygen having 2 to 20 carbon atoms provided that when said carbocyclic group is a norbornane group, one B must be a covalent bond and one B is an unsubstituted alkylene group, wherein each such B which is an unsubstituted alkylene group has 2–20 carbon atoms;

y is 2 to 6, provided that when B has a —C(O)OR$^3$— group attached to A through its carbonyl carbon atom, then y is 3 to 6;

each R$^1$ is independently alkyl containing 1 to 20 carbon atoms or phenyl;

each R$^2$ is independently halogen, alkoxy containing 1 to 20 carbon atoms, phenoxy, acyloxy containing 1 to 20 carbon atoms, or silyloxy;

each R$^3$ is independently an alkylene group containing 2 to 19 carbon atoms; and each n is independently 0, 1 or 2.

DETAILS OF THE INVENTION

Certain terms are used to describe the groups which define the novel compounds disclosed herein. By the term "cycloaliphatic radical" (an "A" group) is meant a saturated group containing one or more carbocyclic rings, which may be fused. Each of the free valencies of this "A" group is to a different carbon atom on the carbocyclic ring that is formed by the "A" group. Preferred "A" groups are cyclohexylene, 2,2-dicyclohexylpropane and norbornylene.

The term "aromatic group" is intended to include rings which often are formally represented as having conjugated double bonds, which rings may be fused. Typical aromatic groups contemplated by this invention are obtained by removing two hydrogen atoms from compounds such as benzene, naphthalene, anthracene, and phenanthrene.

Two carbocyclic A groups may be connected by a covalent bond, by normal or branched alkylene groups (such as, for example, methylene, ethylene, or 2-propylidene groups; or by a heteroatom such as, for example, oxygen or sulfur; or may be fused rings in which two rings share two or more carbon atoms between them.

If B is a covalent bond, then the silicon atom in that particular grouping is bound directly to a carbon atom which is part of a carbocyclic ring.

B may also be an alkylene group containing one or more ether oxygen atoms between alkylene segments, such as (with silicon atom shown also) atoms connected directly to A —OR$^3$— such as —O(CH$_2$)$_m$Si≡, wherein m is 2 to 20, or containing one or more oxygens, O(CH$_2$)$_3$Si≡ or —CH$_2$O(CH$_2$)$_3$Si≡. B may also be an alkylene group containing an ester group between alkylene segments, such as in —CH$_2$O(O)C(CH$_2$)$_m$Si≡, wherein m is an integer of 2 to 18. B may also be —C(O)OR$^3$— such as —C(O)O(CH$_2$)$_m$Si≡, or B may also be —OC(O)R$^3$ such as —O(O)C(CH$_2$)$_m$Si≡, both wherein m is 2 to 18.

In preferred compounds, A is 1,4-cyclohexylene, 2,2'-dicyclohexylpropane, 1,2,4-benzene or

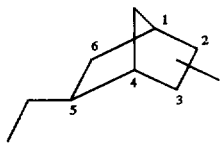

The latter norbornane group is derived from 5-vinyl-2-norbornene and the right-hand bond most probably is attached to the 2 or 3 carbon, or both.

A can also be derived, for example, from biphenyl, from oxydiphenyl, from thiodiphenyl, or from 2,2-diphenylpropane.

In other preferred compounds, n is 0 and/or $R^2$ is halogen (preferably chlorine) or alkoxy. Especially preferred is n-alkoxy containing 1 to 4 carbon atoms, more preferred methoxy or ethoxy, and especially preferred methoxy. $R^2$ may also be oxysilyl. By oxysilyl is meant —OSi≡, wherein the free bonds to silicon (the right-hand bonds) are to groups such as alkyl, alkoxy or another oxysilyl group, for example, $R^1{}_n R^2{}_{3-n}$ as defined above or an oligomeric siloxane containing a series of —Si($R^1$)$_2$OSi($R^1$)$_2$— groups, with up to 10 silicon atoms, preferably 1 to 5 silicon atoms, most preferably 1 to 3 silicon atoms.

If n is not 0, it is preferred $R^1$ is methyl. It is also preferred if y is 2 or 3, especially preferred if it is 2.

Exemplary compounds are as follows:

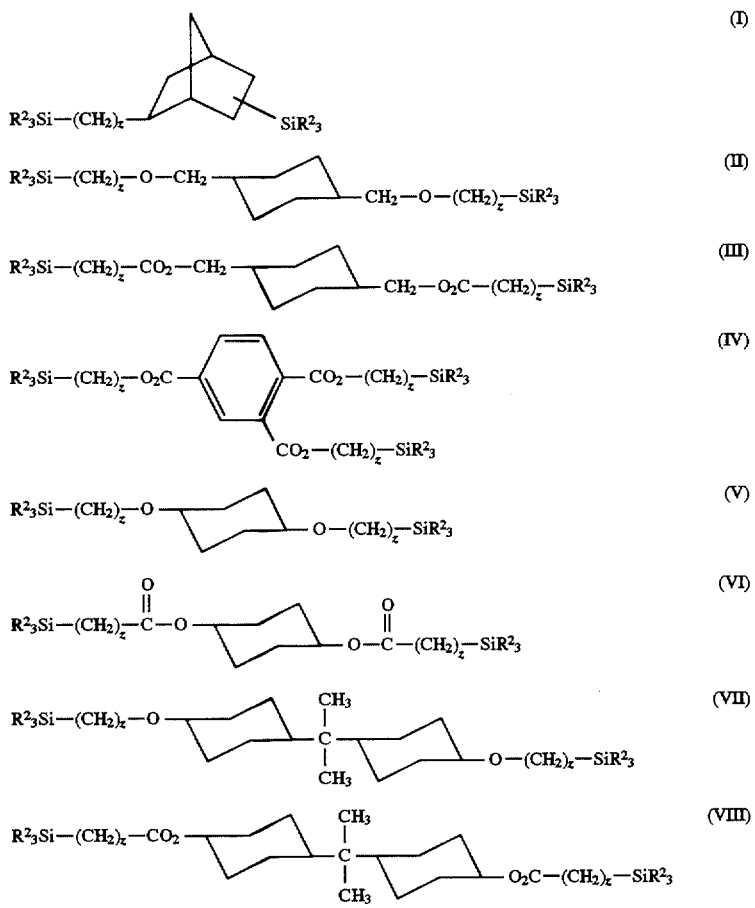

wherein z is 2 to 20 and wherein each B has total up to 20 carbon atoms, and each $R^2$ is independently halogen, alkoxy containing 1 to 20 carbon atoms, phenoxy, acyloxy containing 1–20 carbon atoms, or silyloxy. (There should however be a chain of at least two consecutive carbon atoms attached to the Si in the direction of the "A" group except for (I).) It is also preferred if all of $R^2$ are chloro or methoxy, especially methoxy.

The silicon compounds described herein are often most conveniently made by hydrosilation of an appropriate functional olefin. This hydrostation may be carried out after the functional olefin has been attached in some manner to the cycloaliphatic group, or the hydrosilation may be carried out on the functional olefin and then this silylated compound attached to the carbocyclic group, as by esterification. See the Examples for instances of these types of syntheses. For hydrosilation reactions in general, see E. Y. Lukevits, et at., *Organic Insertion Reactions of Group IV Elements* (Consultants Bureau, New York, 1966) and B. Marciniel, et al., *Comprehensive Handbook on Hydrosilation* (Pergamon Press, Oxford, 1992). As disclosed in these publications, hydrosilation may be accomplished either using free radical initiators or various other catalysts, including transition metal complexes.

Compounds represented by formulas (VII) and (VIII), above, are derived from 2,2-propylidenebis(4-hydroxycyclohexane), which can be made be hydrogenation of Bisphenol A.

The silicon compounds described herein are useful as described above wherein the reactive groups on silicon, such as alkoxy or halo may be hydrolyzed or otherwise reacted to improve adhesion, provide crosslinks, etc. They are especially useful in coatings, where they may be used as reactive materials for the crosslinking of functional group containing (such as hydroxyl functional) polymers. It is believed that these compounds not only provide this "reactive" functionality in coatings, but because of the presence of the cycloaliphatic group provide a good balance of (higher) hardness, flexibility, scratch resistance, and crosslinking speed.

As indicated above, the presently disclosed reactive organosilicon compounds are useful in coatings, especially automotive coatings, either clearcoat or color coat compositions. Such a coating composition, before and/or after application to a substrate, must comprise a film-forming portion, comprising polymeric components, which is referred to as the "binder" or "binder solids" and is dissolved, emulsified or otherwise dispersed in an organic solvent or liquid carrier. The binder solids generally include all the normally solid polymeric non-liquid components of the total composition. Generally, catalysts, pigments, and non-polymeric chemical additives such as stabilizers are not considered part of the binder solids. Non-binder solids other than pigments usually do not amount to more than about 5% by weight of the composition. In this disclosure, the term binder includes the organosilane polymer, the dispersed polymer, and all other optional film-forming polymers.

The applied coating composition suitably contains about 50–100% by weight of the binder and about 0–50% by weight of the organic solvent carrier, not including the compounds of the present invention, which serve a dual function of solvent and binder component. The binder of the coating composition may comprise up to 100% of the reactive organosilicon compounds preferably about 5–80%, more preferably 20–60%, by weight of the binder. The coating composition may optionally also contain a silane-functional polymer, a hydroxy-functional polymer, and/or a dual functional polymer (containing hydroxy functionalities), as for example, disclosed in U.S. Pat. No. 5,244,959 hereby incorporated by reference in its entirety. For example, a silane polymer portion of the binder may have a weight average molecular weight of about 1000–30,000, a number average molecular weight of about 500–10,000. (All molecular weights disclosed herein are determined by gel permeation chromatography using a polystyrene standard.)

Other film-forming and/or crosslinking solution polymers may be included in the present application. Examples include conventionally known acrylics, cellulosics, aminoplasts, urethanes, polyesters, epoxides or mixtures thereof. One preferred optional film-forming polymer is a polyol, for example an acrylic polyol solution polymer of polymerized monomers. Such monomers may include, for example, alkyl acrylates and/or methacrylates and, in addition, hydroxy alkyl acrylates or methacrylates. The polyol polymer preferably has a hydroxyl number of about 50–200 and a weight average molecular weight of about 1,000–200,000 and preferably about 1,000–20,000.

To provide the hydroxy functionality in the polyol, up to about 90% by weight, preferably 20 to 50%, of the polyol comprises hydroxy functional polymerized monomers. Suitable monomers include hydroxy alkyl acrylates and methacrylates, for example, hydroxy ethyl acrylate, hydroxy propyl acrylate, hydroxy isopropyl acrylate, hydroxy butyl acrylate, hydroxy ethyl methacrylate, hydroxy propyl methacrylate, hydroxy is propyl methacrylate, hydroxy butyl methacrylate, and the like, and mixtures thereof.

Other polymerizable non-hydroxy containing monomers may be included in the polyol polymer, in an amount up to about 90% by weight, preferably 50 to 80%. Such polymerizable monomers include, for example, styrene, methylstyrene, acrylamide, acrylonitrile, methacrylonitrile, methacrylamide, methylol methacrylamide, methylol acrylamide, and the like, and mixtures thereof.

Another optional component of the coating composition of the present invention is, in addition to the above polymeric components, a dispersed polymer. Polymers dispersed in an organic (substantially non-aqueous) medium have been variously referred to, in the art, as a non-aqueous dispersion (NAD) polymer, a microgel, a non-aqueous latex, or a polymer colloid. See generally, Poehlin et at., editor, SCIENCE AND TECHNOLOGY OF POLYMER COLLOIDS, Volume 1, pages 40–50 (1983); El-Asser, editor, FUTURE DIRECTIONS IN POLYMER COLLOIDS, pages 191–227 (1987); Barrett, DISPERSION POLYMERIZATION IN ORGANIC MEDIA (John Wiley 1975). See also U.S. Pat. Nos. 4,147,688; 4,180,489; 4,075,141; 4,415,681; and 4,591,533, hereby incorporated by reference. Microgel particles, necessarily cross-linked, have been used for years as impact modifiers for plastics, as theology controllers for coatings, and in basecoats, to permit wet-on-wet application of paints.

Optionally, the present coating composition may further include, particularly in conjunction with an optional polyol polymer, an additional crosslinking agent, for example, conventionally known monomeric or polymeric alkylated melamine formaldehyde resin that is partially or fully alkylated. One preferred crosslinking agent is a methylated and butylated or isobutylated melamine formaldehyde resin that has a degree of polymerization of about 1–3. Generally, this melamine formaldehyde resin contains about 50% butylated groups or is butylated groups and 50% methylated groups. Such crosslinking agents typically have a number average molecular weight of about 300–600 and a weight average molecular weight of about 500–1500. Examples of commercially available resins are "Cymel" 1168, "Cymel" 1161, "Cymel" 1158, "Resimine" 4514 and "Resimine" 354. Preferably, the crosslinking agent is used in the amount of about 5–50% by weight, based on the weight of the binder of the composition. Other crosslinking agents are urea formaldehyde, benzoquanamine formaldehyde and blocked polyisocyanates.

An effective amount of catalyst, typically less than 5% by weight of the composition, is typically added to catalyze the crosslinking of the silane moieties of the silane polymer with itself and with other components of the composition, including the dispersed polymer. Typical of such catalysts are dibutyl tin dilaurate, dibutyl tin diacetate, dibutyl tin dioxide, dibutyl tin dioctoate, tin octoate, aluminum titanate, aluminum chelates, zirconium chelate and the like. Tertiary amines and acids or combinations thereof are also useful for catalyzing silane bonding. Preferably, these catalysts are used in the amount of about 0.1 to 5.0% by weight of the composition.

To improve weatherability of a clear finish produced by the present coating composition, an ultraviolet light stabilizer or a combination of ultraviolet light stabilizers can be added in the amount of about 0.1–5% by weight, based on the weight of the binder. Such stabilizers include ultraviolet light absorbers, screeners, quenchers, and specific hindered amine light stabilizers. Also, an antioxidant can be added, in the about 0.1–5% by weight, based on the weight of the binder.

Typical ultraviolet light stabilizers that are useful include benzophenones, triazoles, triazines, benzoates, hindered amines and mixtures thereof. Specific examples of ultraviolet stabilizers are disclosed in U.S. Pat. 4,591,533, the entire disclosure of which is incorporated herein by reference.

The composition may also include other conventional formulation additives such as flow control agents, for example, such as Resiflow™ S (polybutylacrylate), BYK 320 and 325 (high molecular weight polyacrylates); theology control agents, such as fumed silica; water scavengers such as tetrasilicate, trimethyl orthoformate, triethylorthoformate and the like.

When the present composition is used as a clearcoat (topcoat) over a pigmented colorcoat (basecoat) to provide a colorcoat/clearcoat finish, small amounts of pigment can be added to the clear coat to eliminate undesirable color in the finish such as yellowing.

The present composition also can be pigmented and used as the colorcoat, or as a monocoat or even as a primer or primer surfacer. The composition has excellent adhesion to a variety of substrates, such as previously painted substrates, cold rolled steel, phosphatized steel, and steel coated with conventional primers by electrodeposition. The present composition exhibits excellent adhesion to primers, for example, those that comprise crosslinked epoxy polyester and various epoxy resins, as well as alkyl resin repair primers. The present composition can be used to coat plastic substrates such as polyester reinforced fiberglass, reaction injection-molded urethanes and partially crystalline polyamides.

When the present coating composition is used as a basecoat, typical pigments that can be added to the composition include the following: metallic oxides such as titanium dioxide, zinc oxide, iron oxides of various colors, carbon black, filler pigments such as talc, china clay, barytes, carbonates, silicates and a wide variety of organic colored pigment such as quinacridones, copper phthalocyanines, perylenes, azo pigments, indanthrone blues, carbazoles such as carbazole violet, isoindolinones, isoindolones, thioindigo reds, benzimidazolinones, metallic flake pigments such as aluminum flake and the like.

The pigments can be introduced into the coating composition by first forming a mill base or pigment dispersion with any of the aforementioned polymers used in the coating composition or with another compatible polymer or dispersant by conventional techniques, such as high speed mixing, sand grinding, ball milling, attritor grinding or two roll milling. The mill base is then blended with the other constituents used in the coating composition.

Conventional solvents and diluents may be used, preferably in minimal mounts, to disperse and/or dilute the above mentioned polymers to obtain the present coating composition. Typical solvents and diluents include toluene, xylene, butyl acetate, acetone, methyl isobutyl ketone, methyl ethyl ketone, methanol, isopropanol, butanol, hexane, acetone, ethylene glycol, monoethyl ether, VM and P naphtha, mineral spirits, heptane and other aliphatic, cycloaliphatic, aromatic hydrocarbons, esters, ethers and ketones and the like.

The coating composition can be applied by conventional techniques such as spraying, electrostatic spraying, dipping, brushing, flowcoating and the like. The preferred techniques are spraying and electrostatic spraying. After application, the composition is typically baked at 100°–150° C. for about 15–30 minutes to form a coating about 0.1–3.0 mils thick. When the composition is used as a clearcoat, it is applied over the colorcoat which may be dried to a tack-free state and cured or preferably flash dried for a short period before the clearcoat is applied. The colorcoat/clearcoat finish is then baked as mentioned above to provide a dried and cured finish.

It is customary to apply a clear topcoat over a basecoat by means of a "wet-on-wet" application, i.e., the topcoat is applied to the basecoat without curing or completely drying the basecoat. The coated substrate is then heated for a predetermined time period to allow simultaneous curing of the base and clear coats.

The coating composition can be formulated as a one-package or two-package system that has an extended shelf life.

The following Examples illustrate the invention. All parts and percentages are on a weight basis unless otherwise indicated. In the following examples, the "platinum divinyl complex" is a complex of platinum with divinyltetramethyldisiloxane which contains 2–3% platinum, and is available from Petrarch Silanes and Silicones, Bristol, Pa. 19007, U.S.A. as catalog number PC072.

EXAMPLE 1

Preparation of 5-(2-trichlorosilylethyl)-trichlorosilylnorbornane

To a one-liter, three-necked flask, equipped with a magnetic stirrer, reflux condenser, addition funnel under nitrogen blanket, was added 5-vinyl-2-norbornene (100 g, 0.83 mole). With stirring, the contents of the flask were heated at 75°–85° C., and platinum divinyl complex (0.6 g 2–3% platinum in xylene), and trichlorosilane (320 g, 2.36 moles) were added dropwise over 12 hours. The reaction mixture was heated for additional 36 hours. The excess trichlorosilane was stripped under high vacuum. A gas chromatography analysis showed the product purity to be greater than 94%. Mass spectroscopy (K+IDS) and $^1$H NMR analyses of the product showed that it consisted mainly of 5-(2-trichlorosilylethyl)-trichlorosilylnorbornane, as shown below, with trichlorosilane and 5 vinyl-2-norbornene.

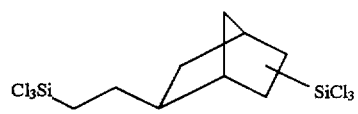

EXAMPLE 2

Preparation of 5-(2-trimethoxylylethyl)-trimethoxysilynorbornane

To the reaction product of Example 1 was added dropwise at such a rate to keep the internal temperature below 30° C. with stirring, a mixture of anhydrous methanol (115 g, 3.6 moles) and trimethylorthoformate (530 g, 5.0 moles) under a vacuum. After the addition was complete, triethylamine (15 g, 0.15 mole) was added and the reaction mixture was refluxed for 2 hours. The volatiles were distilled off. The reaction mixture was distilled at 80°–100° C. under a vacuum 0.03–0.10 Torr, collecting –10% forecut, using a Kugelrohr apparatus. A gas chromatography, mass spectroscopy (K+IDS) and $^1$H NMR analysis indicated the desired structure, as shown below, with > (greater than) 95% purity composed of four isomers in ratio 7/1/3/1 (by GC). Yield: 180 g (59%), colorless liquid, viscosity <0.1 poise at room temperature (rt).

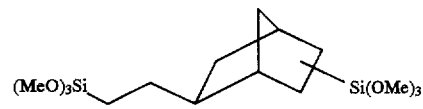

EXAMPLE 3

Preparation of 1,2,4-carboxylic acid, tri-(3-trimethoxysilyl)propyl ester

A mixture of triallyl trimellitate (3 g, 0.009 mole), tri-methoxysilane (6 g, 0.049 mole) and platinum divinyl complex (0.050 g 2–3% platinum in xylene) added over 1 hour in a dry box, was stirred at ft. An exotherm occurred during the catalyst addition. After 4 days the excess tri-methoxysilane was stripped on a rotary evaporator, the reaction system was diluted with 5 mL hexanes, filtered through silica and Darco G-60, volatiles were stripped on a rotary evaporator and under high vacuum. Mass spectroscopy (K+IDS) and $^1$H NMR analysis showed >82% of the desired product, yellow liquid, viscosity 5.3 poise at rt.

EXAMPLE 4

Preparation of 1,4-cyclohexanedimethanol, diundecenoic acid ester

To a one liter flask fitted with a reflux condenser, magnetic stirrer, heating mantle under nitrogen flow connected to HCl trap, was added 10-undecenoic acid (800 g, 4.34 mole) and thionyl chloride (770 g, 6.47 mole). The contents were stirred for 24 hours at rt and heated at ~80° C. for 8 hours. Volatiles were stripped under high vacuum at 60° C. Gas chromatography and ¹H NMR analysis showed essentially pure 10-undecenoic acid chloride. 1,4-Cyclohexanedimethanol (300 g, 2.15 mole) was added slowly to the flask containing the acid chloride and connected to HCl gas trap and the mixture was heated at 80° C. for 48 hours. The reaction mixture was diluted with hexanes, filtered through basic Al₂O₃ and Darco G-60 and volatiles stripped on a rotary evaporator and under high vacuum. ¹H NMR analysis showed the desired 1,4-cyclohexanedimethanol diundecenic acid ester in purity >93%.

EXAMPLE 5

Preparation of 1,4-cyclohexanedimethanol, (di-(11-trimethoxysilyl)undecanoic acid ester A mixture of 1,4-cyclohexanedimethanol, di-(1,1-trimethoxysilyl)-undecanoic acid ester (3 g, 0.006 mole), trichlorosilane (8 g, 0.059 mole) and platinum divinyl complex (0.030 g 2–3% platinum in xylene) added over 1 hour in a dry box, was stirred at rt. An exotherm occurred during the catalyst addition. After 2 days the excess trichlorosilane was stripped on a rotary evaporator. A mixture of anhydrous methanol (1.5 g, 0.047 mole) and trimethylorthofornate (8 g, 0.075 mole) was added slowly at stirring under in a dry box. After 24 hours volatiles were stripped on a rotary evaporator and under high vacuum. ¹H NMR analysis showed no olefin residue and >84% of the Si-CH₂-CH₂-linkage. Product, as shown below, was a yellow liquid, viscosity 0.6 poise at rt.

A compound such as structure (II), shown earlier, can be made by the reaction of allyl bromide and 1,4-cyclohexanedimethanol in the presence of tetrabutylammonium bromide and NaOH to form the diether, followed by hydrosilation with HSiCl₃, followed by reaction with methanol to form the trimethoxysilanes. Procedures similar to those described in the examples may be used.

EXAMPLE 6

Preparation of 1,4-bis[(2-propenyloxy)methyl]cyclohexane

Into a two liter round-bottom three-neck flask equipped with a mechanical stirrer, reflux condensor, thermocouple, and nitrogen inlet, were placed 1,4-cyclohexanedimethanol (375 g, 2.60 moles), allyl bromide (1100 g, 9.09 moles), toluene (830 mL), sodium hydroxide (300 g, 7.5 mole), and tetra-n-butylammonium bromide (110 g, 0.34 mole). The reaction mixture was stirred at 30°–50° C. for 8 hours and at 70°–80° C. for 10 hours. Gas chromatography analysis showed >99% of the desired product. After cooling, the reaction mixture was poured into 2 liters of water, the layers were separated and the aqueous layer was extracted with 150 mL toluene. The toluene solutions were combined and washed with water until pH ~7. The organic phase was dried over anhydrous sodium sulfate, the solvent was stripped on a rotary evaporator and the product was distilled on a Kugelrohr apparatus at 90°–100° C. under a vacuum 0.03 Torr. A gas chromatorgraphy, mass spectroscopy (K⁺IDS) and ¹H NMR analysis indicated the desired structure with >97% purity. Yield: 385 g (66%), colorless liquid.

EXAMPLE 7

Preparation of 1,4-bis[(3-trimethoxysilylpropyloxy)methyl]cyclohexane

A mixture of 1,4-bis[(2-propenyloxy)methyl]cyclohexane (3 g, 0.013 mole), trichlorosilane (10 g, 0.074 mole), platinum divinyl complex (0.14 g 2–3% platinum in xylene) and acetic acid (0.5 g, 0.008 mole) was stirred in a dry box. After 3 days the excess trichlorosilane was stripped on a rotary evaporator. A mixture of anhydrous methanol (1.5 g, 0.047 mole) and trimethylorthoformate (8 g, 0.075 mole) was added slowly at ring in a dry box. After 24 hours volatiles were stripped on a rotary evaporator and under high vacuum. ¹H NMR analysis showed no olefin residue and >75% of the desired Si-CH₂CH₂- linkage. Product was a yellow liquid, viscosity 0.5 poise at rt.

EXAMPLE 8

A composition was made comprising, parts by weight solids, 10.22 parts of a methylated butylated monomeric melamine from Monsanto, 4.64 parts of a trimethylorthoformate water scavenger, 2.32 parts of Tin 384™ UV absorber, 2.20 parts of Tin 123™ hindered amine, 0.40 parts of an acrylic terpolymer solution of Resiflow™ flow modifier, 30.5 parts of a non-aqueous acrylic dispersion as disclosed in commonly assigned U.S. Pat. No. 5,066,698, hereby incorporated by reference in its entirety, 40.21 parts of a dual functional silane-hydroxy resin (consisting of 10% A-174 or methacryloxypropyltrimethoxysilane monomer from Union Carbide, 30% hydroxyethyl methacrylate monomer, 22% cyclohexylmethacrylate monomer, 8% isobutylmethacrylate monomer, and 30% styrene monomer made using Vazo 67™ polymerization initiator in pentanol and ethylene monobutyl ether acetate at about 145° to 150° C. over several hours), 40.9 parts of silanated vinylnorbornane having the structure (I) above with all R⁴ groups being methoxy groups, 0.20 parts of dibutyltindiacetate catalyst, and 2.67 parts of acid catalyst. The composition was 75% by weight solids and 25% by weight solvent. The VOC was 2.20. Thus, a very low VOC high solids clearcoat composition was successfully obtained.

What is claimed is:

1. A compound of the formula

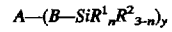

wherein:

A is an organic radical, which is selected from the group consisting of
  (a) carbocyclic groups which are either cycloaliphatic or aromatic and
  (b) two carbocyclic groups which are either cycloaliphatic or aromatic, connected to each other through a covalent bond, or through an alkylene group of 1 to 5 carbon atoms, or through a heteroatom, or fused rings in which two rings share two or more carbon atoms between them;

with y free valencies, each of which free valencies is to a different carbon atom of any carbocyclic ring formed by A; provided that when A belongs to the above group (b), at least two such valencies are attached to two different rings, each B is independently a substituted alkylene group that is substituted with at least one ether oxygen atom and/or at least one ester group, wherein the silicon atom is separated from an oxygen atom by at least two carbon atoms, and wherein the oxygen atom or the ester group which is present as a —C(O)OR³— or —O(O)CR³— group, is connected directly to A or indirectly to A through an alkylene segment; each such B which is substituted with an ester group having 3–20 carbon atoms; each such B which is substituted with the ether oxygen having 2 to 20 carbon atoms;

y is 2 to 6, provided that when B has a —C(O)OR³— group attached to A through its carbonyl carbon atom, then y is 3 to 6;

each R¹ is independently alkyl containing 1 to 20 carbon atoms or phenyl;

each R² is independently halogen, alkoxy containing 1 to 20 carbon atoms, phenoxy, acyloxy containing 1 to 20 carbon atoms, or silyloxy;

each R³ is independently an alkylene group containing 2 to 19 carbon atoms; and each n is independently 0, 1 or 2.

2. The compound as recited in claim 1 wherein A is 1,4-cyclohexylene, 2,2-dicyclohexylpropane, 1,2,4-benzenetriyl or 5-ethylenenorbornylene:

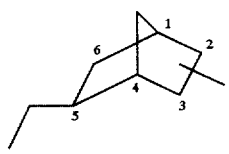

3. The compound as recited in claim 1 wherein n is 0.
4. The compound as recited in claim 2 wherein n is 0.
5. The compound as recited in claim 1 wherein n is 0, and all of R² are chlorine, methoxy, or ethoxy.

6. The compound as recited in claim 4 wherein n is 0, and all of R² are chlorine, methoxy, or ethoxy.

7. The compound as recited in claim 6 wherein n is 0, and all of R² are methoxy.

8. The compound as recited in claim 1, which is selected from the group consisting of:

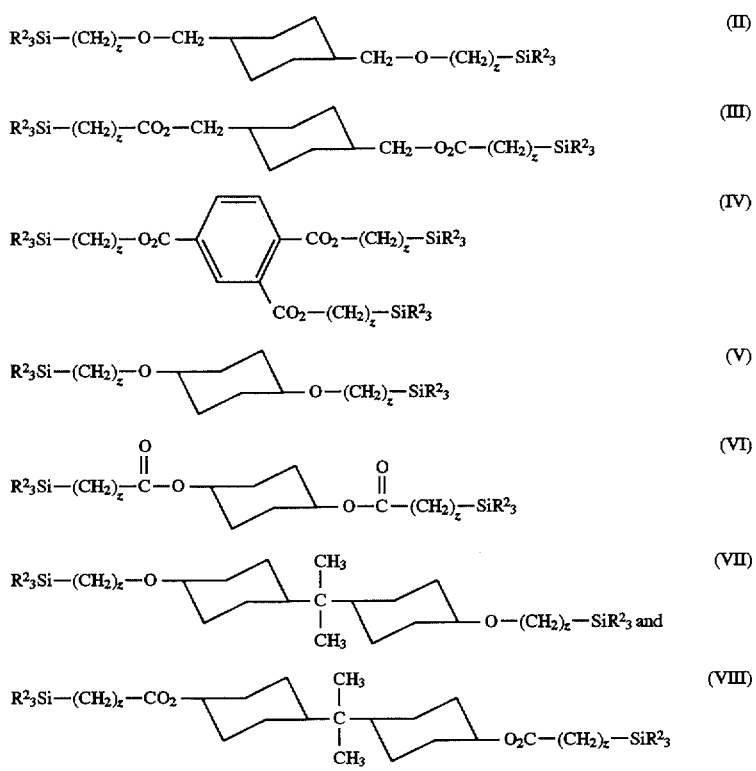

wherein z is 2 to 20, and wherein each B has a total of up to 20 carbon atoms, and each R² is independently halogen, alkoxy containing 1 to 20 carbon atoms, phenoxy, acyloxy containing 1 to 20 carbon atoms, or silyloxy.

9. The compound as recited in claim 8 wherein z is 3 or 10.

10. The compound as recited in claim 8 wherein all R² are chloro or all R² are methoxy.

11. A composition comprising at least one reactive organosilicon compound according to claim 1.

12. The composition of claim 11 further comprising a curable polymer or crosslinker.

13. A process of coating a substrate with a composition of claim 12 comprising applying the composition as a film to the substrate.

14. A compound of the structure:

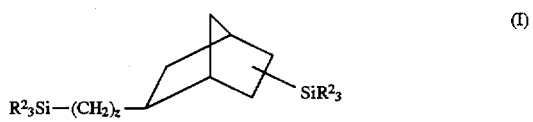

wherein each R² is independently halogen, alkoxy containing 1 to 20 carbon atoms, phenoxy, acyloxy containing 1 to 20 carbon atoms, or silyloxy and wherein z is 2 to 20.

* * * * *